(12) United States Patent
Van Heugten et al.

(10) Patent No.: US 6,551,326 B1
(45) Date of Patent: Apr. 22, 2003

(54) CAPSULORRHEXIS DEVICE

(76) Inventors: Anthony Y. Van Heugten, 10125 Kingsbridge Ave., Tampa, FL (US) 33626; Susan L. Van Heugten, 10125 Kingsbridge Ave., Tampa, FL (US) 33626; Christina J. Van Heugten, 10125 Kingsbridge Ave., Tampa, FL (US) 33626

( * ) Notice: Subject to any disclaimer, the term of this patent is extended or adjusted under 35 U.S.C. 154(b) by 0 days.

(21) Appl. No.: 09/550,949

(22) Filed: Apr. 17, 2000

(51) Int. Cl.$^7$ ................................................ A61B 17/32
(52) U.S. Cl. ...................................... 606/113; 606/166
(58) Field of Search ............................ 606/1, 108, 166, 606/167, 170, 113, 107, 172, 182; 30/272.1, 274, 276, 263, 294, 123.7, 41.8, 41.7

(56) References Cited

U.S. PATENT DOCUMENTS

| | | | |
|---|---|---|---|
| 4,530,359 A | 7/1985 | Helfgott et al. | 128/329 |
| 4,766,897 A | 8/1988 | Smirmaul | 128/305 |
| 5,342,377 A | 8/1994 | Lazerson | 606/166 |
| 5,423,841 A | 6/1995 | Kornefeld | 606/166 |
| 5,728,117 A | 3/1998 | Lash | 606/166 |
| 5,860,994 A | 1/1999 | Yaacobi | 606/166 |

Primary Examiner—Kevin T. Truong
Assistant Examiner—Victor Nguyen

(57) ABSTRACT

A surgical instrument that creates a circular cut 42 of almost any diameter in the lens capsule 50 of the eye, yet its entire diameter is less than 1 mm when inserted into the eye. A cutting edge 14 is affixed to the distal tip of a super-elastic rod 11 with its distal end formed into a circular loop. The circular loop is first retracted inside of an outer tube member 12, and then the tube 12 is inserted into the eye. The loop is then expelled from the tube 12, allowing the loop to reform inside of the eye. As the loop is retracted back into the tube 12, the cutting edge 14 follows the circular path of the loop, cutting a circular opening (a capsulorrhexis) 42, into the lens capsule 50.

3 Claims, 5 Drawing Sheets

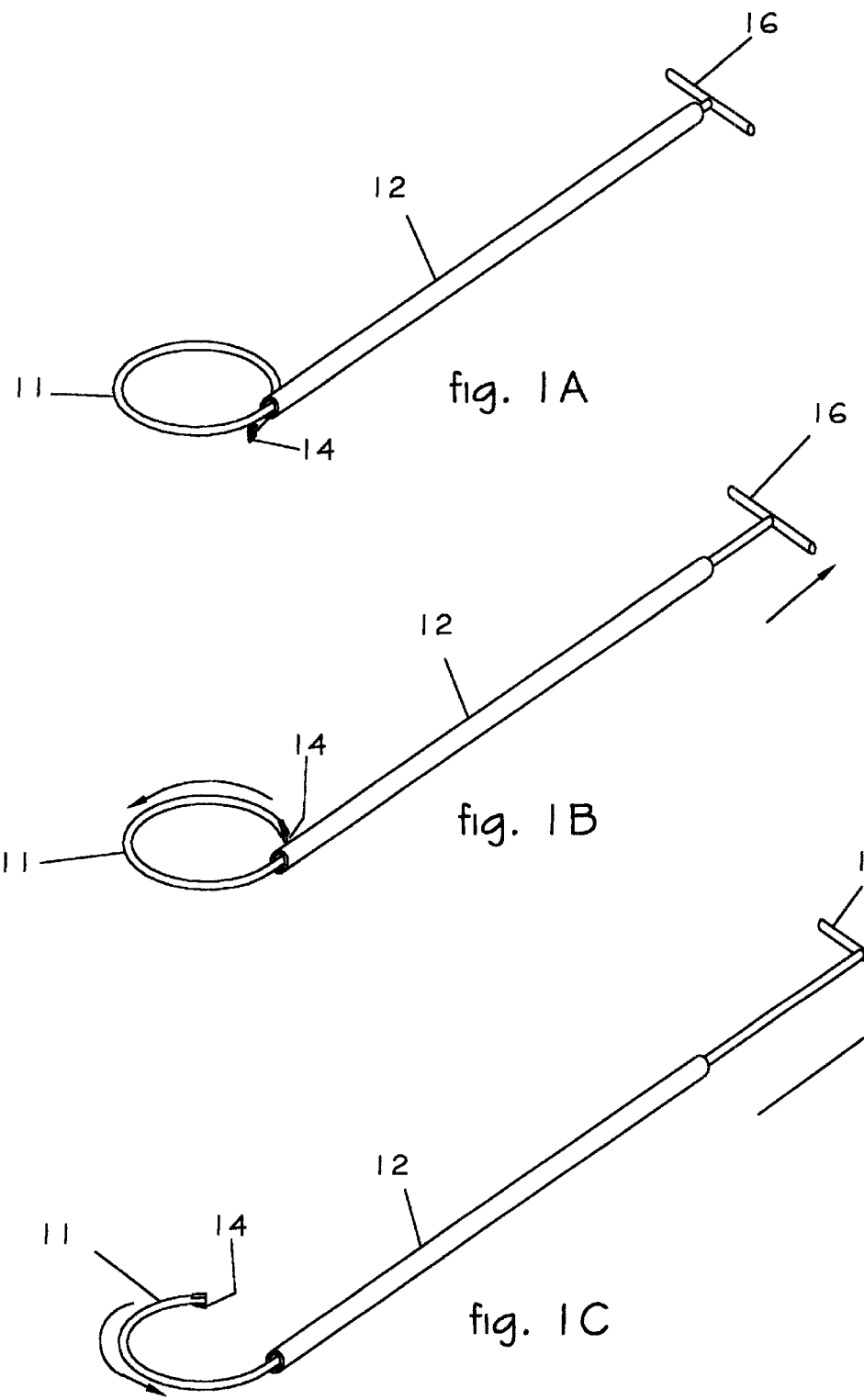

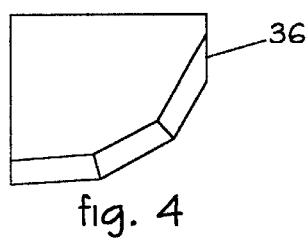
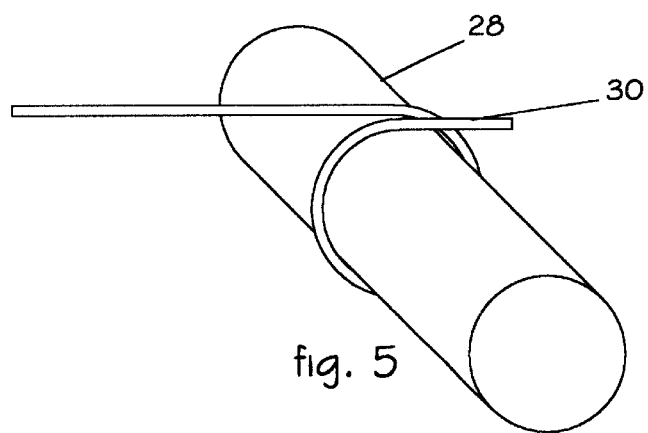
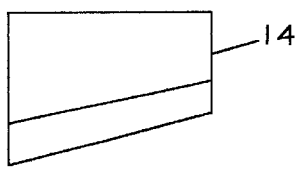
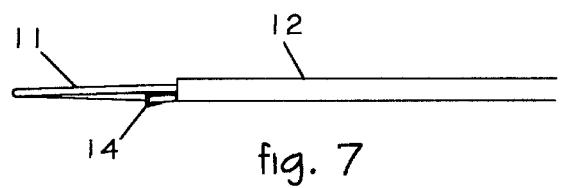
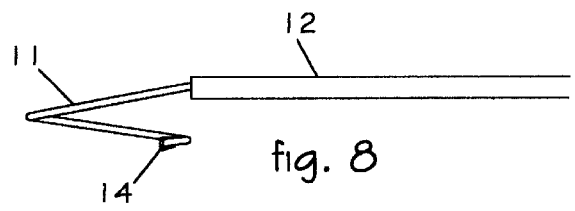
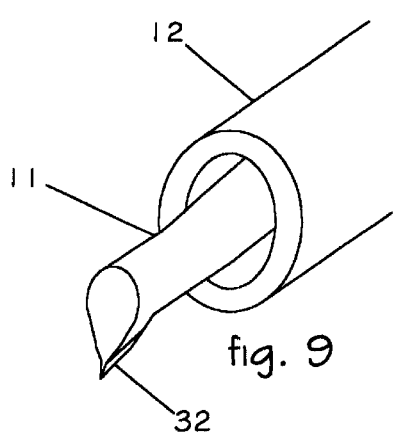
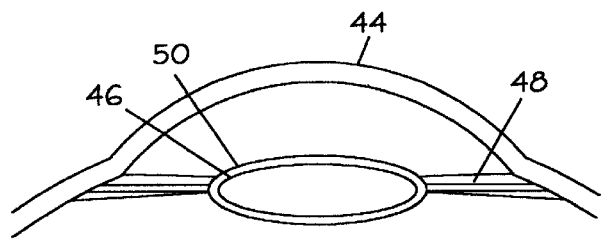

CAPSULORRHEXIS DEVICE

BACKGROUND—FIELD OF THE INVENTION

The present invention relates generally to surgical instruments, and more particularly to providing an instrument for forming a circular opening in the lens capsule of the eye during cataract surgery.

BACKGROUND—DESCRIPTION OF PRIOR ART

In some people, particularly elderly people, the lens inside of the eye grows cloudy. This is referred to as a cataract. The common method of correcting this condition is to remove the natural cloudy lens and replace it with a clear synthetic lens. The natural lens is shaped like a flattened sphere, approximately 9 mm in diameter, and is contained within a capsule. The capsule is suspended radially by countless fine strings, or zonule ligaments, which are connected from the outer periphery of the capsule to the inside surface of the eyeball. In cataract surgery, an incision is made into the eye, and then a circular opening is cut into the lens capsule, typically 6 mm in diameter. (This circular opening cut into the capsule is referred to as the capsulorrhexis.) The natural lens is then broken up into smaller pieces and removed from the capsule and the eye. A synthetic lens is then put into the capsule in place of the natural lens. As this surgical procedure has improved over time, the incision size through which the instruments must pass into the eye has grown smaller and smaller. This smaller incision size contributes to a better surgical outcome due to less disturbance of the spherical shape of the clear dome section of the eye, called the cornea. At the time of this writing, the typical incision size is less than 3 mm. However, the trend is continuing towards even smaller incisions. This small incision size places greater demands for the development of better, smaller instruments.

In order to achieve an optimal surgical result, it is essential that the opening of the capsule be circular, centered, of correct diameter, and without radial tears. Ideally, the cut should be smooth and continuous. The primary techniques currently used to create this opening are the cystotome and the forceps. The cystotome is a needle with the sharp tip bent into a hook. One method of use for the cystotome is to puncture the capsule with the hook, then manipulate the tear with the hook into a generally circular shape. Another cystotome method is to create a series of punctures in a generally circular pattern, then join the punctures by tearing, creating a generally circular shape. In the method used with the forceps, a puncture is first made with a cystotome, then the torn capsule is pulled in various directions with the forceps, guiding the tearing of the capsule in a generally circular direction. Using any of these methods, even the most skilled surgeons can create unpredictable tears. Some tears deviate outward and/or inward from the intended circular path and some have jagged edges that are weak and can tear radially during the stresses put onto the capsule during the insertion of the synthetic lens. Most, if not all, are imperfect circles due to the fact that they were created by freehand movement. Tears that extend within the desired circular shape intrude into the optical zone, impairing vision. This excess material must be removed by a secondary procedure after the eye has healed from the first procedure. Tears that extend beyond the desired circular shape not only detract from a good surgical result, but they can lead to other serious complications such as a ruptured capsule or a decentered lens.

Prior devices have been developed in an attempt to create a consistent, reproducible capsulorrhexis. For example, U.S. Pat. No. 4,766,897 describes a device that mechanically directs a knife in a circular path by means of a guiding loop. The problem with this device is that the guiding loop is too large to enter into the eye through a small incision. In fact, the incision size required is equal to the diameter of the capsulorrhexis, which is not desirable. Other examples include U.S. Pat. No. 4,530,359 which describes a sharpened wire that is deflected sideways out of a tubular member, U.S. Pat. No. 5,423,841 which describes a manually controlled rotating blade, and U.S. Pat. No. 5,342,377 which describes a freely rotating blade mounted on the distal tip of a cannula. The problems associated with these types of devices are that they require the surgeon to manually move the instruments in the desired circular path, resulting not only in imperfect circles, but the motion itself produces damage to surrounding tissue, particularly the endothelium cells (located on the inside of the cornea, and once damaged, will not regenerate). Another example is U.S. Pat. No. 5,728,117 which has a circular blade constrained elliptically within a tube for entry and exit into the eye, which expands into a circle when expelled from the tube. The problems with this device are that no provision is made for the slicing action required to cut the capsule. It relies solely on penetration of a broad edge, requiring excessive downward forces onto the fragile lens capsule structure. Secondly, there are limitations as to how small it can be made, making it impractical for use in the ever-decreasing incision sizes the surgery demands. A final example is U.S. Pat. No. 5,860,994 which describes a knife mounted on a member which is rotated about a central axis, creating a circular capsulorrhexis. The problem with this device is that it has many moving parts, making it difficult to manufacture and to make it small enough to fit within the very small incisions made in modern cataract surgery. Furthermore, instruments with complex moving parts are difficult to clean and sterilize between each use due to body fluids becoming trapped in small cavities.

What is required is a smaller, simpler device, easy to learn how to use, easily cleaned and sterilized that creates smooth, continuous, properly positioned, circular capsulorrhexis cuts that are not dependent upon the accuracy of the freehand movement of the user, and can be inserted, into very small incisions.

SUMMARY OF THE INVENTION

A surgical instrument is presented which creates a circular cut of virtually any diameter in the lens capsule of the eye, yet has a diameter of less than 1 mm when inserted into the eye. A blade is attached to the distal tip of a super-elastic rod. Approximately one quarter of the super-elastic rod (the distal one quarter), is in the shape of a 360 degree loop in its relaxed position. The diameter of the loop is equal to the desired diameter of the circular cut to be made. Prior to inserting the blade into the eye, the super-elastic rod is retracted and contained within an outer tube, which is generally straight. The blade, the straightened loop constrained within the outer tube, and the outer tube are then inserted into the eye through the small incision. Once inside the eye, the loop portion of the super-elastic rod is expelled from the tube, and the super-elastic rod returns to it relaxed, 360 degree loop shape. The loop is then centered over the area where the desired circle is to be cut, and the blade is then pressed into the lens capsule, penetrating it. The super-elastic rod is then retracted back into the tube. As the super-elastic rod retracts, the blade follows in a circular path, cutting the desired circular shape and diameter into the capsule. The looped section of the super-elastic rod performs the circular motion action, and the remaining section is used primarily for grip to impart motion into it, and to provide attachment to the rest of the device. Attachments can be made to the tube and the rod to facilitate handling of these small parts. The super-elastic rod is preferably made from Nitinol, an alloy of 50% nickel and 50% titanium. The cutting blade may be made from any standard knife materials, such as metal, diamond or ceramic. The outer tube can be made of any surgical grade material, such as stainless steel or plastic.

OBJECTS AND ADVANTAGES

Accordingly, several objects and advantages of the present invention are:

(a) to provide a device which the size of the cut made is controlled more by the device, and less by the freehand movement of the user;

(b) to provide a device which the shape of the cut made is controlled more by the device, and less by the freehand movement of the user;

(c) to provide a device that will allow the user to visualize the circular path and position it into the desired location prior to making the cut;

(d) to provide a device that will enable the user to create virtually any size of circular cut, yet enter the confined body space through a very small incision;

(e) to provide a device that will enable the user to easily clean and sterilize the device;

(f) to provide a device with very few moving parts, to increase the reliability of the device;

(g) to provide a device of simple design, enabling a reasonable cost of manufacture using readily available manufacturing methods;

(h) to provide a device of simple theories of operation to allow a user to quickly learn how to use it.

DRAWING FIGURES

In the drawings, closely related figures have the same number but different alphabetical suffixes.

FIGS. 1A to 1E show the device in various stages of extension, with 1A fully extended, and 1E fully retracted.

FIGS. 2A to 2F show the preferred and alternative configurations. FIG. 2A shows the stopping member added to the super-elastic inner tube. FIG. 2B shows the device in the preferred embodiment. FIG. 2C shows the blade mounted onto a member, with the member then mounted to the super-elastic inner rod. FIG. 2D shows a part section of the outer tube cut away with a remaining part section blade guard. FIG. 2E shows the device with a fixation spike added to the outer tubular member. FIG. 2F shows the outer tubular member with a blade parking slot cut into it.

FIGS. 3A to 3G show the logical progress of the use of the instrument in surgery. FIG. 3A shows the device out of the eye. FIG. 3B shows the device in the eye. FIG. 3C shows the device being extended. FIG. 3D shows the device fully extended. FIG. 3E shows the device partially retracted and the capsulorrhexis partially cut. FIG. 3F shows the device fully retracted and the capsulorrhexis fully cut. FIG. 3G shows the device out of the eye, and the capsulorrhexis fully cut.

FIG. 4 shows an alternative blade design example.

FIG. 5 shows the loop being formed into the super-elastic inner rod.

FIG. 6 shows the preferred blade design.

FIG. 7 shows the loop from a side view, with little or no downward spiral formation.

FIG. 8 shows the loop from the side view, with a downward spiral formation.

FIG. 9 shows the super-elastic inner rod with a blade formed directly into it.

FIG. 10 is a side view of the eye, illustrating the major components of the eye related to this device.

Figure 1D:
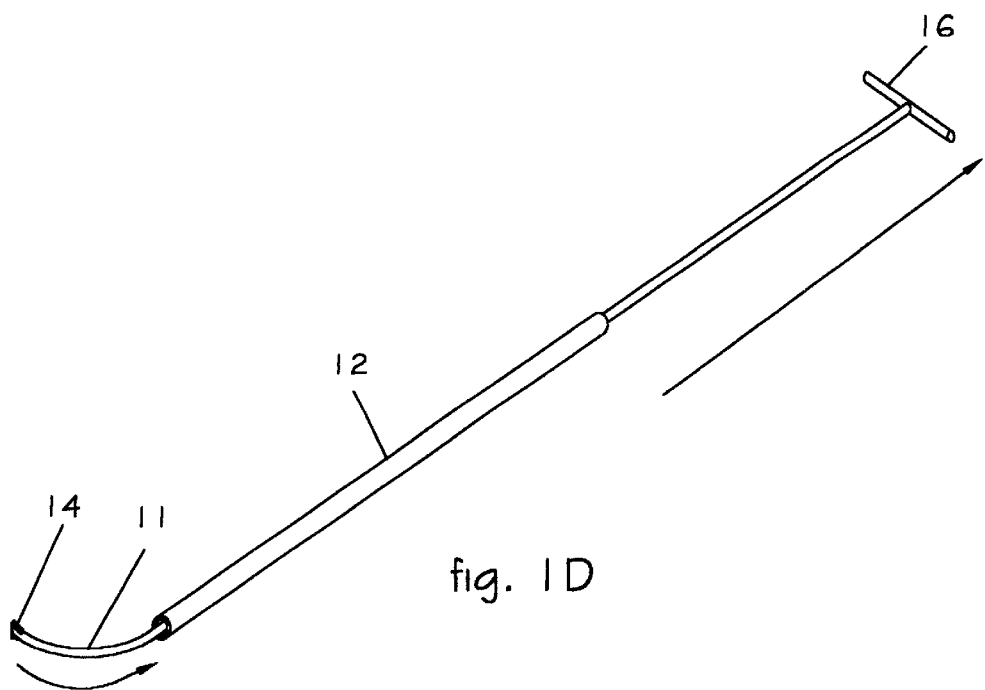
Figure 1E:
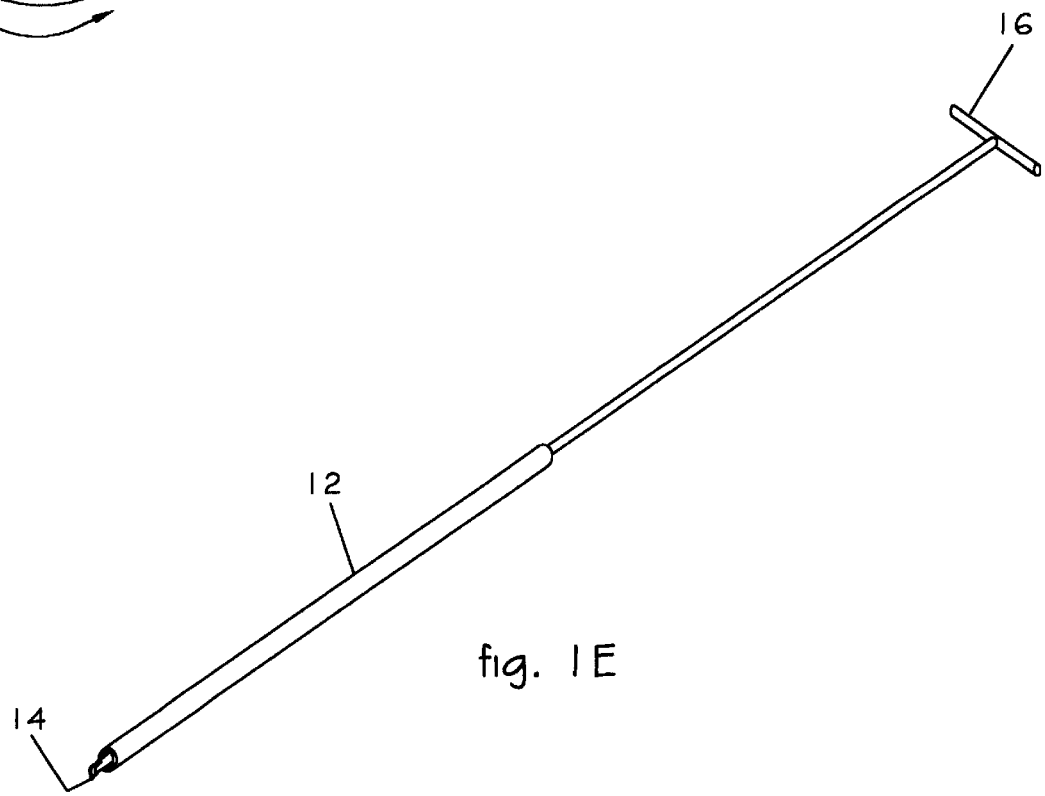

REFERENCE NUMERALS IN DRAWINGS 11 super-elastic rod inner member
14 blade
18 stopping member
22 fixation spike
26 blade parking slot
30 super-elastic rod loop being formed
36 alternative blade
40 eye
44 cornea
48 zonule ligaments
12 tubular outer member
16 handle grip
20 blade mount member
24 blade guard
28 loop forming mandrel
32 sharpened distal tip
38 incision
42 capsulorrhexis cut
46 lens capsule
50 lens

Description-FIGS. 1A THRU 1E, 2B, 6 And 7- Preferred Embodiment

A preferred embodiment of the present invention is illustrated in FIGS. 1A thru 1E, 2B, 6 and 7. A super-elastic rod inner member 11 has a circular loop that can repeatably be confined into a straight shape, and when released, returns to its circular loop shape without losing the memory of that circular shape. A slot is cut into the distal tip of the rod 11, and a blade 14 is mounted into the slot. The straight section of the rod 11 is positioned inside of a tubular outer member 12.

When the circular loop section of the rod 11 is retracted inside of the tube 12, the circular loop section straightens to conform to the inside shape of the tube 12. The width of the device in this position is now considerably less than the width of the circular loop, allowing insertion and withdrawal through a small incision.

Once inserted into an eye, the loop section of the rod 11 is expelled from the tube 12, and the loop reforms into its natural, circular loop shape. As the rod 11 is again retracted back into the tube 12, the blade 14 follows a circular path, incising a circular cut into the surface that the blade 14 makes contact with.

Description-FIGS. 1A, 2A, 2C, 2D, 2E and 2F- Additional Embodiments

Figure 2A:
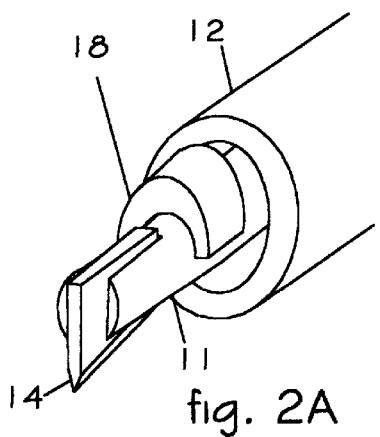
Figure 2B:
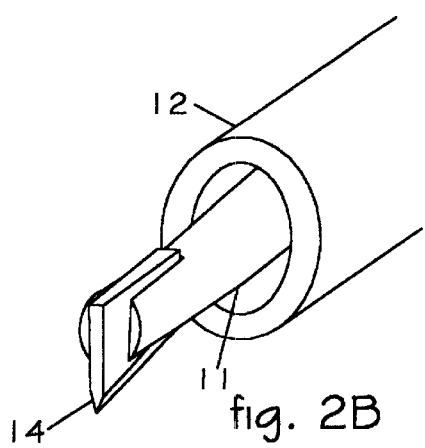
Figure 2C:
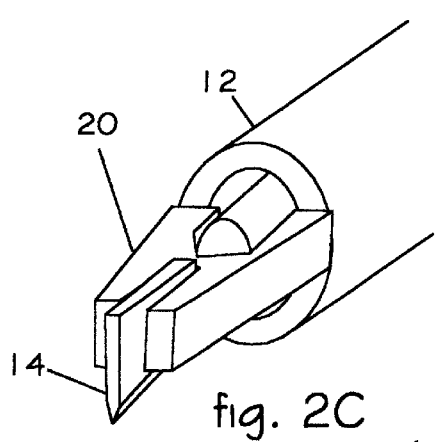
Figure 2D:
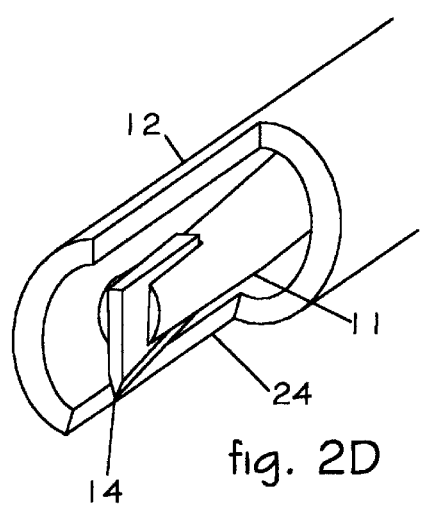
Figure 2E:
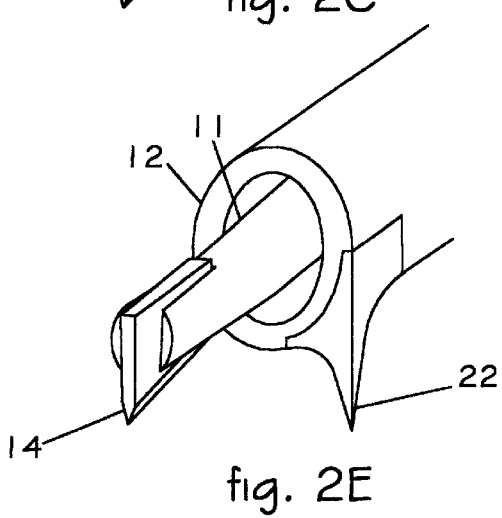
Figure 2F:
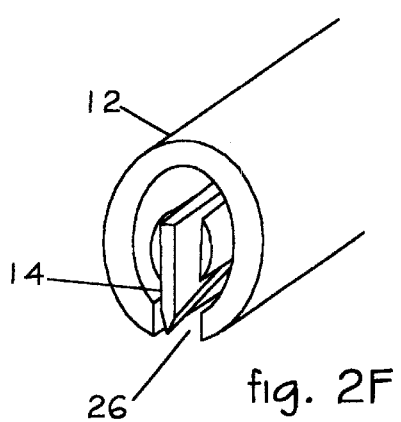

Additional embodiments are shown in FIGS. 1A, 2A, 2C, 2D, 2E and 2F. In FIG. 1A, an additional handle grip member 16 is added to the super-elastic rod inner member 11 to facilitate gripping. In FIG. 2A, an additional stopping member 18 is added to the rod 11 to prevent the blade from contacting the tubular outer member 12 and becoming damaged. In FIG. 2C, the blade is mounted onto a blade mount member 20, which in turn is mounted onto the rod 11. In FIG. 2D, half, or more of a section of the tube 12 is removed, leaving a partial section of tube 12 as a blade guard 24. In FIG. 2E, a fixation spike 22 is added to the distal tip of tube 12, providing a means to hold the eye in place while the capsulorrhexis cut is being made. In FIG. 2F, a slot is cut into the tube 12 to create a blade parking slot 26 to provide a protected space within which the blade 14 can be parked while not in use, or during entry and exit into and out of the eye.

Description-FIGS. 4, 8 and 9-Alternative Embodiments

There are various possibilities with regard to the blade and loop configuration. FIG. 4 shows an alternative blade 36 with multiple cutting facets. FIG. 8 shows the super-elastic inner rod member 11 with a downward spiral. This will allow the user to enter into the eye at an angle, rather than on a plane parallel to the plane of the circle to be cut. This can occur when the patient has an extended eyebrow bone, or in the case of use where the instrument is used in a body cavity other than the eye. FIG. 9 shows a blade 32 as being formed from the distal tip of the rod 11, making the blade an integral part of the rod 11.

Description-FIG. 5-Forming the Circular Loop

The size and shape of the circular loop is important since the circular capsulorrhexis cut will be the same size and shape. To make the loop, wrap a Nitinol wire 30, around a mandrel 28, with the mandrel having the desired diameter and shape of the loop, as shown in FIG. 5. Then, heat the wire 30 and the mandrel 28 at the time and temperature specified by the supplier of the Nitinol. In our example, we heated the wire 30 and mandrel 28 at 900 degrees F. for ten minutes in an oxygen free environment. Our Nitinol wire was purchased from Small Parts, Inc., in Miami Fla.

Description-FIG. 10-Pertinent Components of the Eye

FIG. 10 shows a side view of the eye. A cornea is shown as item 44. A lens capsule is shown as item 50. A lens inside of the capsule 50, is shown as item 46. Zonule ligaments are shown as item 48.

Operation-FIGS. 3A, 3B, 3C, 3D, 3E, 3F and 3G

Figure 3A:
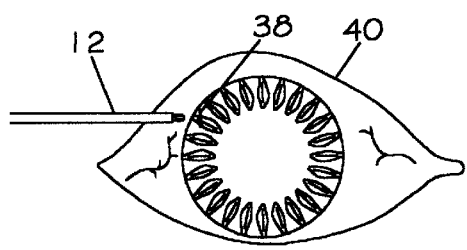

The manner of using the capsulorrhexis instrument is as follows:

(a) Retract the super-elastic rod inner member (hidden inside of the device) inside of the outer tubular member 12, FIG. 3A.

Figure 3B:
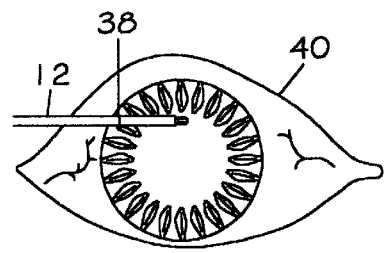

(b) Insert the retracted instrument into an incision 38 made into an eye 40 shown in FIG. 3B. If no blade guard is employed, rotate the entire instrument 90 degrees before insertion. After insertion, rotate back to the position of the blade pointing down. This will prevent the blade from slicing the incision.

Figure 3C:
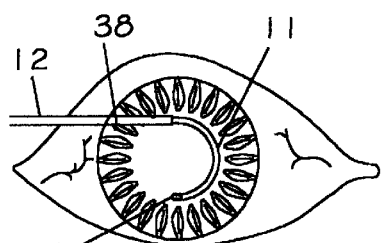
Figure 3D:
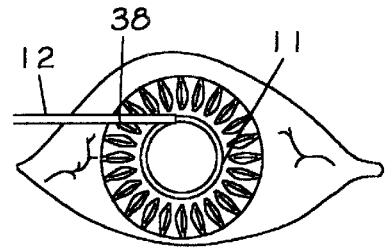

(c) Advance the super-elastic rod inner member 11 fully, as shown in FIGS. 3C and 3D.

(d) Position the loop, which is formed by rod 11, in the desired location, shown in FIG. 3D.

(e) Press downward so that the blade 14 penetrates the surface to be cut.

Figure 3E:
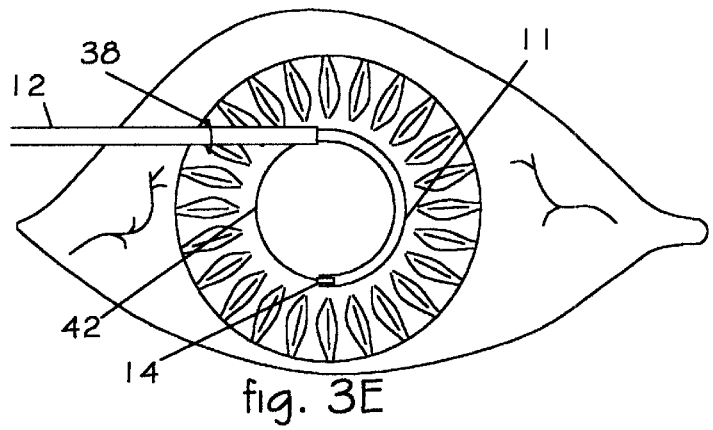
Figure 3F:
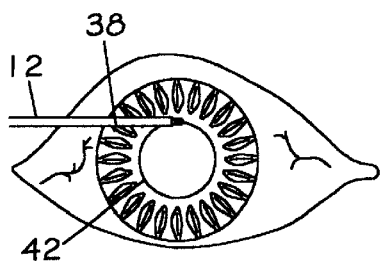

(f) Retract the rod 11 into the tube 12, which results in a circular capsulorrhexis cut 42 as shown in FIG. 3E and 3F.

(g) If no blade guard is employed, rotate the instrument 90 degrees.

Figure 3G:
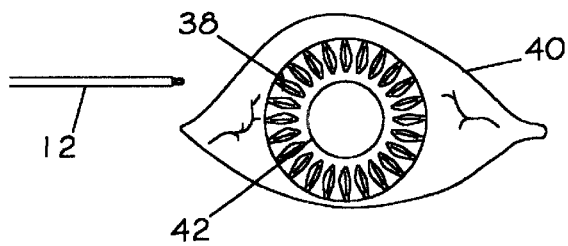

(h) Remove the instrument from the eye, as shown in FIG. 3G.

Advantages

From the description above, a number of advantages of our capsulorrhexis device become evident:

(a) The size of the circle cut is predetermined by the size of the loop rather than by the freehand motion of the user. Thus, the size of the circle cut is more precise, selectable and repeatable.

(b) The shape of the circle cut is predetermined by the shape of the inner loop rather than by the freehand motion of the user. Thus, the shape of the circle is more precise and repeatable.

(c) The position of the circle can be visualized before the cut is made, rather than during the cutting. This results in a more controlled positioning of the circle.

(d) The device can be configured to cut virtually any size circle, as determined by the size of the loop created, yet the instrument can be inserted through a very small incision that is only a small fraction of the diameter of the circle to be cut.

(e) The device has only one simple, straight path inside of the tubular outer member where fluids are not easily trapped. This single straight path is easily cleaned by simple flushing while advancing and retracting the super-elastic rod inner member in and out of the tubular outer member, resulting in a quick, low risk cleaning and sterilization operation.

(f) The device has only the super-elastic rod inner member sliding inside of the tubular outer member as moving parts, leaving very few moving parts to fail. This results in a very reliable device.

(g) The device has very few parts, each being very simple and each capable of being produced by readily available manufacturing methods. This results in a very cost effective manufacturing process.

(h) The theory of operation is so simple that it can be understood and mastered with little training. This results in a very short learning period for the user.

Conclusions, Ramifications, and Scope

Accordingly, the reader will see that the capsulorrhexis device of this invention can be used to reliably create more accurate, predictable, consistent circular cuts, yet gain access to the surface within the confined body space requiring the cut, through a very small incision. In addition, the device is of such simple design, its manufactured cost will be reasonable, its cleaning and sterilization will be easy, and the reliability of the device will be high. Furthermore, the simplicity of its function will enable a very short learning period for the user, allowing them to quickly provide an improved surgical outcome to the millions of people who undergo procedures requiring such cuts each year.

Although the description above contains many specifications, these should not be construed as limiting the scope of the invention but as merely providing illustrations of some of the presently preferred embodiments of this invention. For example, the cutting edge of the knife could have other shapes such as concave, convex, etc., the cutting edge of the blade could be facing the distal tip rather than away from it, the outer tubular member could be oval, square, etc, the outer tubular member could be curved rather than straight, the loop could be oval, spiral, square, or some other shape, etc., and further appendages may be added to both the inner and outer members to facilitate gripping and motion. Additionally, the examples of use given are primarily related to eye surgery, but the device could be used in other surgical procedures requiring a circular cut such as inside the heart, bladder, intestines, arteries, etc.

Thus, the scope of the invention should be determined by the appended claims and their legal equivalents, rather than by the examples given.

What is claimed is:

1. A device for making a circular cut into a lens capsule of an eye, comprising:
   A. a tubular, substantially straight outer member, having a distal end and a proximal end;
   B. an inner member comprising a super elastic rod having a distal end and a proximal end;
      (1) said inner member being slidably, partially enclosed within said outer member;
      (2) said inner member having means attached thereto for sliding its distal end in and out of said distal end of said outer member, whereby said inner member is constrained to be substantially straight when said distal end of said inner member is constrained within said outer member, and whereby said distal end of said inner member forms a circular loop when unconstrained and extended from said distal end of said outer member;
   C. cutting means having a cutting edge attached to said distal end of said inner member;
      (1) said cutting edge being disposed so as make a circular cut when said distal end of said inner member is retracted into said distal end of said outer member from said unconstrained state;
      (2) said cutting means not being substantially larger than said distal end of said outer member;
   whereby said distal end of said outer member, with said distal end of said inner member retracted therewithin, may be inserted into an eye through an incision substantially the same size as said distal end of said outer member, and said distal end of said inner member may then be extended within the eye from said distal end of said outer member so as to form said circular loop.

2. A device for making a circular cut into a lens capsule of an eye, comprising:
   A. a tubular, substantially straight outer member, having a distal end and a proximal end;
   B. an inner member comprising a super elastic rod having a distal end and a proximal end;
      (1) said inner member being slidably, partially enclosed within said outer member;
      (2) said inner member having means attached thereto for sliding its distal end in and out of said distal end of said outer member, whereby said inner member is constrained to be substantially straight when said distal end of said inner member is constrained within said outer member, and whereby said distal end of said inner member forms a circular loop when unconstrained and extended from said distal end of said outer member;
   C. cutting means having a cutting edge attached to said distal end of said inner member;
      (1) said cutting edge being disposed so as make a circular cut when said distal end of said inner member is extended out from and beyond said distal end of said outer member and from said constrained state;
      (2) said cutting means not being substantially larger than said distal end of said outer member;
   whereby said distal end of said outer member, with said distal end of said inner member retracted therewithin, may be inserted into an eye through an incision substantially the same size as said distal end of said outer member, and said distal end of said inner member may then be extended within the eye from said distal end of said outer member so as to form said circular loop.

3. A device for making a circular cut, comprising:
   a tubular outer member having an open distal end,
   a rod inner member made from an elastic spring material,
   said rod inner member having a distal end,
   said rod inner member having a substantially circular loop in its distal end when said rod inner member is in a relaxed, unconstrained and unsupported state,
   a blade attached to the distal tip of said circular loop in said rod inner member such that said blade is supported by and held in space by said rod inner member,
   said rod inner member being partially enclosed and slidable within said tubular outer member such that when said circular loop in said rod inner member is extended beyond the open distal end of said tubular outer member, said circular loop is unconstrained and unsupported by said tubular member,
   and such that as said circular loop in said rod inner member is retracted within said outer tubular member, said circular loop in said rod inner member deforms into the shape of the inside of said tubular outer member along the portion of the length of said tubular outer member that said rod inner member is within, causing said blade supported by and held in space by said rod inner rod member to move along a substantially circular path of motion being created by the unsupported and unconstrained portion of the circular loop not yet within said outer tubular member,
   and such that as said circular loop in the distal end of said rod inner member is being expelled from the open distal end of said tubular outer member and said circular loop becomes no longer constrained and supported by said outer tubular member, the distal tip of said circular loop that is supporting in space said blade causes said blade to travel along a circular path created by the circular motion of the unsupported portion of said circular loop as said rod inner member reforms into said circular loop,
   whereby the user may create a circular cut.

* * * * *